United States Patent [19]

Masaki et al.

[11] Patent Number: 5,312,811
[45] Date of Patent: May 17, 1994

[54] PEPTIDE DERIVATIVES AND ANTIDEMETIA AGENTS

[75] Inventors: Mitsuo Masaki, Chiba; Seiji Kondo, Saitama; Norihisa Miyake, Saitama; Masaki Uehara, Saitama; Kenji Hirate, Saitama; Yoshikazu Isowa, Tokyo; Yoshiaki Sato, Tokyo; Yoshiharu Nakashima, Tokyo, all of Japan

[73] Assignees: Nippon Chemiphar Co., Ltd.; Fujirebio Kabushiki Kaisha, Tokyo, Japan

[21] Appl. No.: 393,515

[22] Filed: Aug. 14, 1989

[30] Foreign Application Priority Data

Aug. 12, 1988 [JP] Japan ................... 63-201356
Apr. 15, 1989 [JP] Japan ................... 1-95920

[51] Int. Cl.$^5$ .................... A61K 37/02; C07K 5/10; C07K 7/06
[52] U.S. Cl. ........................ 514/16; 514/17; 530/317; 530/329; 530/330
[58] Field of Search .................. 530/315–317, 530/329–330; 514/16, 17

[56] References Cited

FOREIGN PATENT DOCUMENTS 0354820 2/1990 European Pat. Off. .

OTHER PUBLICATIONS

Yasuo, H. "Synthesis and Properties of S-Aminomethylthiamine and N-Hydroxmethylthiamine", Chem. Pharm. Bull. 24(5) pp. 845-849, (1976).

Kovacs, et al, A Major Metabolite of Arginine Vasopressin in the Brain is a Highly Potent Neuropeptide, Science, 221, pp. 1310-1312 (1983).

Yasuo et al, "The reaction of S-aminomethylthiamine with Acid Anhydride-The synthesis of O,S-bis-(α-aminoacyl) thiamine", Chem. Pharm. Bull. 1976, 24(5) 852-8 Chemical Abstracts, 85 (15) 108605v.

Primary Examiner—Merrell C. Cashion, Jr.
Assistant Examiner—S. G. Marshall
Attorney, Agent, or Firm—McAulay Fisher Nissen Goldberg & Kiel

[57] ABSTRACT

A novel peptide derivative having the formula:

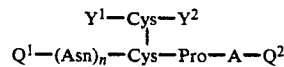

wherein A between Pro and $Q^2$ is Arg or Lys: $Q^1$ is pGlu or H; $Q^2$ is —Gly—OH or OH; $Y^1$ is H or —CO—T and $Y^2$ is OH or T; wherein T is a thiamine derivative group is disclosed. The peptide derivative shows a remarkable nootropic effect.

9 Claims, No Drawings

PEPTIDE DERIVATIVES AND ANTIDEMETIA AGENTS

BACKGROUND OF THE INVENTION

1. Field of the Invention

The present invention relates to novel peptide derivatives having a nootropic effect and antidementia agent containing the same.

2. Description of Prior Art

Vasopressin has been previously known as a compound having a nootropic effect, i.e., intelligence developing effect. Recently, it has been reported that a peptide seemingly corresponding to a vasopressin fragment, for example, one having the following formula:

$$\begin{array}{c} pGlu-Asn-Cys-Pro-Arg-Gly-NH_2 \\ | \\ H-Cys-OH \end{array}$$

has such a nootropic effect as that of vasopressin in Science, 221, pp. 1310–1312 (1983).

Further, Brain Research, 371, 17(1986) describes that a peptide having the formula:

$$\begin{array}{c} H-Asn-Cys-Pro-Arg-OH \\ | \\ H-Cys-OH \end{array}$$

also has a nootropic effect.

SUMMARY OF INVENTION

It is an object of the present invention to provide new peptide derivatives having a nootropic effect which is superior to the known vasopressin as well as to the known peptides corresponding to vasopressin fragments.

The present invention provides a novel peptide derivative having the formula (I):

$$\begin{array}{c} Y^1-Cys-Y^2 \\ | \\ Q^1-(Asn)_n-Cys-Pro-A-Q^2 \end{array} \quad (I)$$

wherein
A between Pro and $Q^2$ is Arg or Lys: $Q^1$ is pGlu or H; $Q^2$ is —Gly—OH or OH; $Y^1$ is H or —CO—T and $Y^2$ is OH or T; wherein T represents a group having the formula (II):

$$-O-CH_2CH_2-\underset{\underset{R^1S}{|}}{C}=\underset{\underset{CHO}{|}}{C}-N-CH_2-\!\!\!\underset{N}{\overset{\overset{H_2N}{\diagup}\overset{N}{\diagdown}}{\diagdown\!\!\!\diagup}}\!\!-CH_3 \quad (II)$$

wherein $R^1$ is a group selected from the group consisting of an alkylcarbonyl group having 2 to 7 carbon atoms, an arylcarbonyl group having 7 to 10 carbon atoms and an alkylthio group having 1 to 6 carbon atoms, or
a group having the formula (III):

$$R^2-O-CH_2CH_2-\underset{\underset{-S}{|}}{\overset{\overset{CH_3}{|}}{C}}=\underset{\underset{CHO}{|}}{C}-N-CH_2-\!\!\!\underset{N}{\overset{\overset{H_2N}{\diagup}\overset{N}{\diagdown}}{\diagdown\!\!\!\diagup}}\!\!-CH_3 \quad (III)$$

wherein $R^2$ is a group selected from the group consisting of hydrogen, an alkylcarbonyl group having 2 to 7 carbon atoms, and an arylcarbonyl group having 7 to 10 carbon atoms, and at least either $Y^1$ or $Y^2$ contains the group T, n is 0 or 1; and amino acids constituting the peptide are those of type L with the proviso that Pro and Arg may be those of type D, and its functional derivative.

The novel peptide derivatives of the invention can be in the form of their pharmaceutically acceptable salts.

The above-mentioned peptide derivatives, their functional derivatives, and their pharmaceutically acceptable salts show a prominent nootropic effect in passive avoidance tests using rats, and are prominently effective as active component of pharmaceutical agent for prevention or treatment of senile dementia (Alzheimer's dementia), cerebrovascular dementia and other dementia diseases.

DETAILED DESCRIPTION OF THE INVENTION

The peptide derivatives of the present invention have the aforementioned formula (I) and may be in the form of their functional derivatives.

Examples of the peptide derivatives of the formula (I) according to the present invention have the following formulae:

$$\begin{array}{c} H-Cys-T \\ | \\ H-Asn-Cys-Pro-Arg-OH \end{array}$$

$$\begin{array}{c} H-Cys-T \\ | \\ H-Asn-Cys-Pro-Arg-NH_2 \end{array}$$

$$\begin{array}{c} H-Cys-T \\ | \\ pGlu-Asn-Cys-Pro-Arg-OH \end{array}$$

$$\begin{array}{c} H-Cys-T \\ | \\ H-Asn-Cys-Pro-Arg-Gly-NH_2 \end{array}$$

$$\begin{array}{c} H-Cys-T \\ | \\ pGlu-Asn-Cys-Pro-Arg-Gly-NH_2 \end{array}$$

$$\begin{array}{c} H-Cys-T \\ | \\ pGlu-Asn-Cys-Pro-D-Arg-Gly-NH_2 \end{array}$$

$$\begin{array}{c} H-Cys-T \\ | \\ pGlu-Asn-Cys-D-Pro-Arg-Gly-NH_2 \end{array}$$

$$\begin{array}{c} H-Cys-T \\ | \\ pGlu-Asn-Cys-Pro-Lys-Gly-NH_2 \end{array}$$

$$\begin{array}{c} H-Cys-T \\ | \\ pGlu-Cys-Pro-Arg-Gly-NH_2 \end{array}$$

In the above formulae, "T" preferably is $T^1$ which is a group of the formula (II) wherein $R^1$ is benzoyl.

Examples of the functional derivatives of the peptide derivatives of the formula (I) include the following derivatives:

a) N-acyl derivatives having N-acyl group(s) at the functional group(s); N-acyl group is derived from an aliphatic carboxylic acid having 1 to 6 carbon atoms, preferably one derived from acetic acid; the N-acyl group can be expressed by —NHCOR (wherein R is an alkyl group having 1-5 carbon atoms), b) derivatives having, at the functional group(s), groups in the form of amides, or monoalkyl or dialkyl substituted-amides having alkyl chain(s) of 1 to 6 carbon atoms; which can be expressed by —CONH$_2$, —CONHR, and —CONR$_2$ (wherein R is an alkyl group having 1-6 carbon atoms), and c) derivatives having, at the functional group(s) in the form of esters derived from alcohol having 1 to 18 carbon atoms, preferably those derived from an aliphatic alcohol having 1 to 6 carbon atoms; which can be expressed by —COOR (wherein R is an alkyl group having carbon 1-18 atoms, preferably 1-6 carbon atoms).

As the examples of pharmaceutically acceptable salts of the peptide derivatives of the invention or their derivatives, acid addition salts and basic salts such as alkali metal salts and ammonium salts can be mentioned. Examples of such acid addition salts include salts of inorganic acids (e.g., hydrochloric acid, sulfuric acid and phosphoric acid) or of organic acids (e.g., acetic acid, propionic acid, citric acid, tartaric acid, malic acid, oxalic acid and methanesulfonic acid). Examples of basic salts include sodium salt, potassium salt, and triethylamine salt.

In the specification, the peptides are described by abbreviations commonly used in the field of chemistry, or abbreviations recommended by the IUPAC-IUB Commission on Biochemical Nomenclature. For example, the following symbols are used in the specification. The amino acids should be construed to be of the L-type, unless specific description with respect to optical configuration is given.

Asn: asparagine
Arg: arginine
Cys: cysteine
Gly: glycine
pGlu: pyroglutamic acid
Lys: lysine
Pro: proline
Boc: t-butoxycarbonyl
Z: benzyloxycarbonyl
Mbs: p-methoxybenzenesulfonyl
MBzl: p-methoxybenzyl
Acm: Acetamidomethyl
Scm: S-carbomethoxysulfenyl
OBzl: benzyl ester
OSu: N-hydroxysuccinimide ester The compounds of the present invention can be prepared by the methods conventionally employed in peptide chemistry. For example, they can be prepared by those processes described in Schröder and Lübke, *The Peptides*, Vol 1, Academic Press, New York, 1965. and Nobuo Izumiya et al., *Fundamental and Experiment of Peptide Synthesis*, Maruzen, Tokyo, 1985, and can be prepared by either the solution synthesis or the solid phase synthesis.

The thiamine group of the formula (II) or (III) can be introduced into the peptide by reacting a cysteine derivative having a thiamine group with a mercapto group contained in the side chain of the cysteine of the obtained peptide skeleton to form a disulfide bond. Otherwise, the compounds of the invention can be prepared through peptide-forming condensation reaction using a cystine derivative having a thiamine group as a peptide skeleton-forming amino acid.

Examples of the methods for formation of the peptide bonds include azide method, acid chloride method, symmetrical anhydride method, mixed anhydride method, N,N'-dicyclohexylcarbodiimide method, N,N'-dicyclohexylcarbodiimido-additive method, activated ester method, carbonyldiimidazole method, oxidation-reduction method, and the one employing a Woodward reagent K.

In the synthesis of peptide, the cystine moiety which is an amino acid forming the peptide of the invention can be formed by employing a cystine derivative or by converting a cysteine moiety of the peptide chain into a cystine moiety after the formation of the peptide chain by the conventional method.

Before carrying out the coupling reaction, carboxyl group, amino group, guanidino group and mercapto group and the like which do not participate in the reaction can be protected, and those which participate in the coupling reaction can be activated, both by the methods well known in the art.

Examples of the protecting groups for the carboxyl group include ester-forming groups such as methyl, ethyl, benzyl, p-nitrobenzyl, t-butyl and cyclohexyl.

Examples of the protecting groups for the amino group include benzyloxycarbonyl, t-butoxycarbonyl, isobornyloxycarbonyl, and 9-fluorenylmethyloxycarbonyl.

Examples of the protecting groups for the guanidino group include nitro, benzyloxycarbonyl, tosyl, p-methoxybenzenesulfonyl, and mesitylensulfonyl.

Examples of the protecting groups for the mercapto group include trityl, acetamidomethyl, benzyl, p-methoxybenzyl, and 3-nitro-2-pyridinesulfenyl.

Examples of the activation of carboxyl group include symmetrical anhydride, mixed anhydride, azide and active ester (ester with alcohol e.g., pentachlorophenol, 2,4-dinitrophenol, cyanomethyl alcohol, p-nitrophenol, N-hydroxysuccinimide, N-hydroxy-5-norbornene-2,3-dicarboxyimide, N-hydroxyphthalimide, and 1-hydroxybenzotriazol). An example of the activation of amino group is phosphite-amide.

The reaction is generally carried out in a solvent such as chloroform, dichloromethane, ethyl acetate, N,N-dimethylformamide, dimethylsulfoxide, pyridine, dioxane, tetrahydrofuran, water, methanol and mixture of these solvents.

The reaction temperature may be in the range of approx. —30° C. to 50° C., which is generally employed for the reaction.

The condition for removing the protecting group of the peptide of the invention may differ depending on the kind of the blocking group, but it should be the one which is able to release the blocking group without giving any influence to the peptide bonding.

The protecting group can be removed by acid treatment, for example, treatment with hydrogen chloride, hydrogen bromide, hydrogen fluoride, methanesulfonic acid, trifluoromethanesulfonic acid, trifluoroacetic acid, and mixture of these acids. Further, the reduction with sodium metal in liquid ammonia or catalytic hydrogenolysis over palladium-carbon can be employed. On the reaction for removing the protecting group by the above acid treatment, addition of cation scavenger such as anisole, phenol and thioanisole is advantageous.

After the reaction is complete, the prepared peptide of the present invention can be obtained by the conventional process for purification of peptides, for example, extraction, partition, reprecipitation, recrystallization or column chromatography.

Further, the peptides of the present invention can be converted into their functional derivatives or their pharmaceutically acceptable salts as described above by the conventional manner.

The peptide derivatives of the invention show a strong nootropic effect in passive avoidance tests using rats as described hereinafter.

The peptide derivatives of the invention are effective to the following diseases, and can be employed for prevention or treatment thereof: senile dementia (Alzheimer's dementia), cerebrovascular dementia, and dementia based on Alzheimer's disease, Pick's disease, Huntington's disease, Creutzfeldt-Jakob disease, Parkinson's disease, cerebellar myelic denatured disease.

The peptide derivatives of the invention have an extremely low toxicity, and does not cause no death even by administration at extremely higher dose than its effective dose.

The peptide derivatives of the invention may be in the form of their derivatives, or salt thereof. No matter their forms are, the dose as amount of the peptide derivative of the formula (1) is preferably in the range of 0.1 ng/day to 100 μg/day. In the case of parenteral administration (excluding rectal administration), the dose preferably is in the range of 10 ng/day to 100 μg/day. In the case of oral administration and rectal administration, it is preferable that the dose should be 10 to 100 times to that of the parenteral administration (excluding rectal administration). The peptide derivative of the invention is mainly administered parenterally (e.g., intravenous or hypodermic injection, intracerebroventricular or intraspinal administration, nasal administration, and rectal administration). It can be also administered orally depending on the case.

The peptide derivatives of the invention can be incorporated into pharmaceutical compositions in the form of injection liquid, suppository, powder, collunarium, granule and tablets. The peptide derivatives of the invention can be preserved as a physiological saline solution or can be freeze-dried in an ampule after addition of mannitol or sorbitol and is melted when it is used for administration.

Examples of the invention are set forth hereinafter.

In each example, the eluants used for a thin-layer chromatography (TLC) were as follows. As for the solid phase, TLC Plate Silica Gel 60F$_{254}$ by Merck Co., Ltd. was used.

$Rf^1$: chloroform-methanol-acetic acid-water (80:20:2.5:5) lower layer
$Rf^2$: chloroform-methanol-water (70:30:5)
$Rf^3$: n-butanol-acetic acid-water (2:1:1)

Further, purification by a high-performance liquid chromatography was carried out using the following materials:

Column: μBondapak $C_{18}$ 1.9 ×15 cm
Mobile phase:
A) 0.05% trifluoroacetic acid (TFA)
B) acetonitrile

REFERENCE EXAMPLE 1

Preparation of H-Cys(Scm)-T$^1$ hydrochloride (T$^1$ is a group of the formula (II) wherein R$^1$ is benzoyl)

(1) Preparation of Boc-Cys(Acm)-T$^1$

To a solution of 1.0 g of Boc-Cys(Acm)-OH, 1,3g of S-benzoylthiamine, and 20 mg of 4-dimethylaminopyridine in 50 ml of dichloromethane was dropwise added under chilling with ice a solution of 0.78 g of N,N'-dicyclohexylcarbodiimide in 5 ml of dichloromethane. The resulting mixture was further stirred for 30 min. under chilling with ice and then for one hour at room temperature. The produced N,N'-dicyclohexylurea was removed by filtration, and the filtrate was washed with saturated aqueous sodium hydrogencarbonate and water. The washed filtrate was dried over anhydrous sodium sulfate, and then treated to distill off the solvent. The residue was treated with ether to give the desired compound as a crystalline product.

Yield: 1.8 g
M.P.: 71°–75° C.
$Rf^1$: 0.74
$Rf^2$: 0.82
$[\alpha]_D$: −39.2° (c=0.5, DMF)

(2) Preparation of Boc-Cys(Scm)-T$^1$

To a solution of 600 mg of Boc-Cys(Acm)-T$^1$ in 6 ml of methanol-dichloromethane (1:1, v/v) was added 0.14 ml of carbomethoxysulfenyl chloride (Cl-Scm) and the resulting mixture was stirred for 20 min. at room temperature. The mixture was then treated to distill off the solvent and purified using silica gel column and chloroform-methanol eluant to give the desired compound as an oil.

Yield: 580 mg
$Rf^1$: 0.82
$Rf^2$: 0.88 $[\alpha]_D$: −44.0° (c=0.5, DMF)

(3) Preparation of H-Cys(Scm)-T$^1$ hydrochloride 470 mg of Boc-Cys(Scm)-T$^1$ was placed in 2 ml of 4N HCl-ethyl acetate for 30 min. at room temperature, and then the solvent was distilled off. The residue was purified using silica gel column and chloroform-methanol eluant to give the desired compound as an oil.

Yield: 250 mg
$Rf^1$: 0.38
$Rf^2$: 0.54 $[\alpha]_D$: −38.4° (c=0.5, DMF)

EXAMPLE 1:

Preparation of

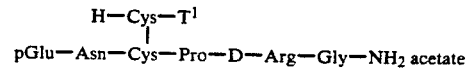

pGlu—Asn—Cys—Pro—D—Arg—Gly—NH$_2$ acetate (1) Preparation of Z-D-Arg(Mbs)-Gly-NH$_2$ In a mixture of 500 ml of ethyl acetate and 200 ml of 5% aqueous citric acid was dissolved under stirring 30 g of Z-D-Arg(Mbs)-OH dicyclohexylamine salt. The ethyl acetate portion was washed with water and dried over anhydrous sodium sulfate. The solvent was distilled off. The residue was dissolved in 300 ml of N,N-dimethylformamide (DMF). To the DMF solution were added under chilling with ice 5 g of H-Gly-NH$_2$ hydrochloride, 5 ml of N-methylmorpholine, 8 g of 1-hydroxybenzotriazole and 9.8 g of N,N'-dicyclocarbodiimide. The mixture was stirred for 18 hours at room temperature. The produced N,N'-dicyclohexylurea was removed by filtration, and DMF was distilled off. The residue was dissolved in a mixture of 2-butanol and dichloromethane (5:1, v/v). The resulting solution was washed successively with saturated aqueous sodium hydrogencarbonate, dilute hydrochloric acid saturated with sodium chloride, and saturated aqueous sodium chloride, and then dried over anhydrous sodium sulfate. The solvent was distilled off. The residue was treated with methanol-ether to give the desired compound as a crystalline product.

Yield: 14.6 g
M.P.: 194°–196° C.
$Rf^1$: 0.24
$Rf^2$: 0.52 $[\alpha]_D$: −2.9° (c=0.5, DMF)

(2) Preparation of Boc-Pro-D-Arg(Mbs)-Gly-$NH_2$

A solution of 10.7 g of Z-D-Arg(Mbs)-Gly-$NH_2$ in 200 ml of 80% acetic acid was stirred for 6 hours in a stream of hydrogen in the presence of 10% palladium-carbon. The palladium-carbon was then removed by filtration and the solvent was distilled off from the filtrate. The residue was dried under reduced pressure and then dissolved in 100 ml of DMF. To the resulting solution were added 3 ml of N-methylmorpholine and 6.2 g of Boc-Pro-OSu, and the mixture was stirred for 18 hours at room temperature. DMF was distilled off. The residue was dissolved in a mixture of 2-butanol and dichloromethane (5:1, v/v). The resulting solution was washed successively with saturated aqueous sodium hydrogencarbonate, dilute hydrochloric acid saturated with sodium chloride, and saturated aqueous sodium chloride, and then dried over anhydrous sodium sulfate. The solvent was distilled off. The residue was treated with ether to give the desired compound as a crystalline product.

Yield: 11.9 g
M.P.: 108°–111° C.
$Rf^1$: 0.32
$Rf^2$: 0.56 $[\alpha]_D$: −6.9° (c=0.5, DMF)

(3) Preparation of Boc-Cys(MBzl)-Pro-D-Arg(Mbs)-Gly-$NH_2$ 2.9 g of Boc-Pro-D-Arg(Mbs)-Gly-$NH_2$ was placed in 25 ml of 4N HCl-ethyl acetate for 30 min. at room temperature, and then the solvent was distilled off. The residue was dissolved in 50 ml of DMF. To the DMF solution were added under chilling with ice 0.53 ml of N-methylmorpholine, 1.8 g of Boc-Cys(MBzl)-OH, 0.85 g of 1-hydroxybenzotriazole and 1.1 g of N,N'-dicyclocarbodiimide. The mixture was stirred for 18 hours at room temperature. The produced N,N'-dicyclohexylurea was removed by filtration, and DMF was distilled off. The residue was dissolved in a mixture of 2-butanol and dichloromethane (5:1, v/v). The resulting solution was washed succesively with saturated aqueous sodium hydrogencarbonate, dilute hydrochloric acid saturated with sodium chloride, and saturated aqueous sodium chloride, and then dried over anhydrous sodium sulfate. The solvent was distilled off. The residue was treated with ether to give the desired compound as a crystalline product.

Yield: 3.3 g M.P.: 127°–130° C.
$Rf^1$: 0.47
$Rf^2$: 0.63 $[\alpha]_D$: −7.6° (c=1.0, DMF)

(4) Preparation of Z-pGlu-Asn-Cys(MBzl)-Pro-D-Arg(Mbs)-Gly-$NH_2$ 3.18 g of Boc-Cys(MBzl)-Pro-D-Arg(Mbs)-Gly-$NH_2$ was placed in 20 ml of 4N HCl-ethyl acetate for 30 min. at room temperature, and then the solvent was distilled off. To the residue were added a mixture of 2-butanol and dichloromethane (5:1, v/v) and saturated aqueous sodium hydrogencarbonate. The organic portion was taken out, washed with saturated aqueous sodium chloride and dried over anhydrous sodium sulfate. The solvent was distilled off, and the residue was dissolved in 30 ml of DMF. To the DMF solution were added under chilling with ice 1.77 g of Z-pGlu-Asn-OH, 0.63 g of 1-hydroxybenzotriazole and 0.97 g of N,N'-dicyclocarbodiimide. The mixture was stirred for 18 hours at room temperature. The produced N,N'-dicyclohexylurea was removed by filtration, and DMF was distilled off. The residue was dissolved in a mixture of 2-butanol and dichloromethane (5:1, v/v). The resulting solution was washed successively with saturated aqueous sodium hydrogencarbonate, dilute hydrochloric acid saturated with sodium chloride, and saturated aqueous sodium chloride, and then dried over anhydrous sodium sulfate. The solvent was distilled off. The residue was treated with ether to give the desired compound as a crystalline product.

Yield: 3.4 g M.P.: 143°–145° C.
$Rf^1$: 0.24
$Rf^2$: 0.45 $[\alpha]_D$: −25.6° (c=1.0, DMF)

(5) Preparation of:

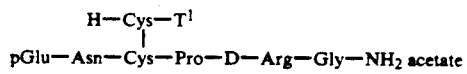

pGlu—Asn—Cys—Pro—D—Arg—Gly—$NH_2$ acetate

To a mixture of 0.2 ml of anisole and 2 ml of methanesulfonic acid was added 200 mg of Z-pGlu-Asn-Cys(MBzl)-Pro-D-Arg(Mbs)-Gly-$NH_2$. The mixture was stirred for 1 hour at room temperature and, after addition of ether, the supernatant portion was removed. The precipitate was dissolved in water. The solution was subjected to Dowex 1×2 (acetate type) treatment, and freeze-dried.

The freeze-dried residue was dissolved in 5 ml of 0.05% trifluoroacetic acid, and to the solution was added under chilling with ice 88 mg of H-Cys(Scm)-$T^1$ hydrochloride obtained in the aforementioned Reference Example 1. The mixture was stirred for 20 min. and then purified by high-performance liquid chromatography at 12 ml/min. (flow rate), 0 to 10% B) 20 min. linear gradient (mobile phase), subjected to Dowex 1×2 (acetate type) treatment and freeze-dried to obtain the desired compound.

Yield: 104 mg $Rf^3$: 0.08 $[\alpha]_D$: −41.6° (c=0.6, water)

EXAMPLE 2

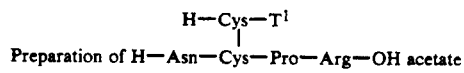

Preparation of H—Asn—Cys—Pro—Arg—OH acetate

The desired compound was prepared from 27 mg of H-Asn-Cys-Pro-Arg-OH acetate and 31 mg of H-Cys(Scm)-$T^1$ hydrochloride prepared in Reference Example 1, in the same manner as in Example 1-(5).

Yield: 18 mg $Rf^3$: 0.07 $[\alpha]_D$: −60.7° (c=0.5, water)

EXAMPLE 3

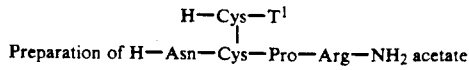

Preparation of H—Asn—Cys—Pro—Arg—$NH_2$ acetate

The desired compound was prepared from 97 mg of H-Asn-Cys-Pro-Arg-$NH_2$ acetate and 49 mg of H-

Cys(Scm)-T¹ hydrochloride prepared in Reference Example 1, in the same manner as in Example 1-(5).
Yield: 49 mg Rf³: 0.06 [α]_D: −54.6° (c=0.5, water)

EXAMPLE 4

Preparation of pGlu—Asn—Cys—Pro—Arg—OH acetate

The desired compound was prepared from 32 mg of pGlu-Asn-Cys-Pro-Arg-OH acetate and 32 mg of H-Cys(Scm)-T¹ hydrochloride prepared in Reference Example 1, in the same manner as in Example 1-(5).
Yield: 33 mg Rf³: 0.11 [α]_D: −65.1° (c=0.5, water)

EXAMPLE 5

Preparation of H—Asn—Cys—Pro—Arg—Gly—NH₂ acetate

The desired compound was prepared from 65 mg of H-Asn-Cys-Pro-Arg-Gly-NH₂ acetate and 60 mg of H-Cys(Scm)-T¹ hydrochloride prepared in Reference Example 1, in the same manner as in Example 1-(5)
Yield: 42 mg Rf³: 0.05 [α]_D: −57.0° (c=0.5, water)

EXAMPLE 6

Preparation of pGlu—Asn—Cys—Pro—Arg—Gly—NH₂ acetate
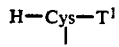

The desired compound was prepared from 28 mg of pGlu-Asn-Cys-Pro-Arg-Gly-NH₂ acetate and 27 mg of H-Cys(Scm)-T¹ hydrochloride prepared in Reference Example 1, in the same manner as in Example 1-(5).
Yield: 25 mg Rf³: 0.10 [α]_D: −66.4° (c=0.5, water)

EXAMPLE 7

Preparation of pGlu—Asn—Cys—Pro—Lys—Gly—NH₂ acetate
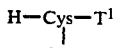

The desired compound was prepared from 67 mg of pGlu-Asn-Cys-Pro-Lys-Gly-NH₂ acetate and 50 mg of H-Cys(Scm)-T¹ hydrochloride prepared in Reference Example 1, in the same manner as in Example 1-(5).
Yield: 35 mg Rf³: 0.22 [α]_D: −51.9° (c=0.6, water)

EXAMPLE 8

Preparation of pGlu—Asn—Cys—D—Pro—Arg—Gly—NH₂ acetate

(1) Preparation of Z-Arg(Mbs)-Gly-NH₂
The desired compound was prepared from 10 g of Z-Arg(Mbs)-OH dicyclohexylamine salt, 1.7 g of H-Gly-NH₂ hydrochloride, 1.7 ml of N-methylmorpholine, 2 g of 1-hydroxybenzotriazole and 3.4 g of N,N'-dicyclocarbodiimide in the same manner as in Example 1-(1).
Yield: 5.0 g M.P.: 201°–202° C.
Rf¹: 0.26
Rf²: 0.55 [α]_D: +2.1° (c=0.5, DMF)

(2) Preparation of Boc-D-Pro-Arg(Mbs)-Gly-NH₂
The desired compound was prepared from 5.2 g of Z-Arg(Mbs)-Gly-NH₂, 3.1 g of Boc-D-Pro-OSu, and 2.2 ml of N-methylmorpholine in the same manner as in Example 1-(2).
Yield: 5.7 g M.P.: 88°–91° C.
Rf¹: 0.35
Rf²: 0.59 [α]_D: +8.7° (c=0.6, DMF)

(3) Preparation of Boc-Cys(MBzl)-D-Pro-Arg(Mbs)-Gly-NH₂
The desired compound was prepared from 5.0 g of Boc-D-Pro-Arg(Mbs)-Gly-NH₂, 3.4 g of Boc-Cys(MBzl)-OH, 2.3 ml of N-methylmorpholine, 1.5 g of 1-hydroxybenzotriazole and 2.1 g of N,N'-dicyclocarbodiimide in the same manner as in Example 1-(3).
Yield: 3.8 g M.P.: 101°–103° C.
Rf¹: 0.47
Rf²: 0.63 [α]_D: −16.4° (c=1.0, DMF)

(4) Preparation of Z-pGlu-Asn-Cys(MBzl)-D-Pro-Arg(Mbs)-Gly-NH₂
The desired compound was prepared from 3.5 g of Boc-Cys(MBzl)-D-Pro-Arg(Mbs)-Gly-NH₂, 1.6 g of Z-pGlu-Asn-OH, 0.46 ml of N-methylmorpholine, 0.75 g of 1-hydroxybenzotriazole and 0.92 g of N,N'-dicyclocarbodiimide in the same manner as in Example 1-(4).
Yield: 3.1 g M.P.: 147°–149° C.
Rf¹: 0.25
Rf²: 0.50 [α]_D: −24.6° (c=1.0, DMF)

(5) Preparation of:

pGlu—Asn—Cys—D—Pro—Arg—Gly—NH₂ acetate
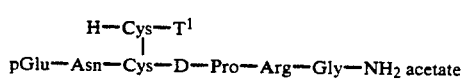

The desired compound was prepared from 200 mg of Z-pGlu-Asn-Cys(MBzl)-D-Pro-Arg(Mbs)-Gly-NH₂ and 60 mg of H-Cys(Scm)-T¹ hydrochloride obtained in the Reference Example 1 in the same manner as in Example 1-(5).
Yield: 54 mg Rf³: 0.08 [α]_D: −21.4° (c=0.6, water)

EXAMPLE 9

Preparation of pGlu—Cys—Pro—Arg—Gly—NH₂ acetate
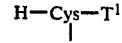

(1) Preparation of Boc-Cys(MBzl)-Pro-Arg(Mbs)-Gly-NH₂
3.7 g of Boc-Pro-Arg(Mbs)-Gly-NH₂ was placed in 20 ml of 4N HCl-ethyl acetate for 30 min. at room temperature, and then the solvent was distilled off. The residue was dried under reduced pressure and dissolved in 50 ml of DMF. To the DMF solution were added under chilling with ice 0.7 ml of N-methylmorpholine, 2.1 g of Boc-Cys(MBzl)-OH, 0.85 g of 1-hydroxybenzotriazole and 1.4 g of N,N'-dicyclocarbodiimide. The mixture was stirred for 18 hours at room temperature. The produced N,N'-dicyclohexylurea was removed by filtration and DMF was distilled off. The residue was dissolved in chloroform. The resulting solution was washed successively with saturated aqueous sodium hydrogencarbonate, dilute hydrochloric acid saturated with sodium chloride, and saturated aqueous sodium chloride, and then dried over anhydrous sodium sulfate. The solvent was distilled off. The residue was treated with ether to give the desired compound as a crystalline product.

Yield: 3.2 g
M.P.: 104°–107° C.
Rf$^1$: 0.44
Rf$^2$: 0.63 [α]$_D$: −27.9° (c=0.5, DMF)

(2) Preparation of Z-pGlu-Cys(MBzl)-Pro-Arg(Mbs)-Gly-NH$_2$

The desired compound was prepared from 2.5 g of Boc-Cys(MBzl)-Pro-Arg(Mbs)-Gly-NH$_2$, 10 ml of 4N HCl-ethyl acetate, 0.4 ml of N-methylmorpholine and 1.1 g of Z-pGlu-OSu in the same manner as in Example 1-(4).

Yield: 2.8 g
M.P.: 108°–112° C.
Rf$^1$: 0.22
Rf$^2$: 0.52 [α]$_D$: −36.0° (c=1.0, DMF)

(5) Preparation of:

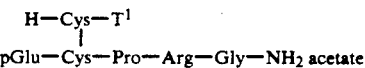

pGlu—Cys—Pro—Arg—Gly—NH$_2$ acetate

To a mixture of 0.2 ml of anisole and 2 ml of methanesulfonic acid was added 140 mg of Z-pGlu-Cys(MBzl)-Pro-Arg(Mbs)-Gly-NH$_2$. The mixture was stirred for 1 hour at room temperature and, after addition of ether, the supernatant portion was removed. The precipitate was dissolved in water. The solution was subjected to Dowex 1×2 (acetate type) treatment, and freeze-dried.

The freeze-dried residue was dissolved in 5 ml of 0.05% trifluoroacetic acid, and to the solution was added under chilling with ice 33 mg of H-Cys(Scm)-T$^1$ hydrochloride obtained in the Reference Example 1. The mixture was stirred for 20 min. and then purified by high-performance liquid chromatography at 12 ml/min. (flow rate), 0 to 10% B) 20 min. linear gradient (mobile phase), subjected to Dowex 1×2 (acetate type) treatment and freeze-dried to obtain the desired compound.

Yield: 32 mg
Rf$^3$: 0.10 [α]$_D$: −58.7° (c=0.5, water)

Examples of pharmacological tests showing the effectiveness of the peptide derivatives of the present invention are set forth below.

Pharmacological Test: Examination on Improvement Effect of Experimental Retrograde Amnesia by Cycloheximide The effect of peptide derivatives of the invention on memory consolidation was evaluated by conducting one-trial passive avoidance experiment using male Wistar rats in accordance with the method described by Burbach et al., Science, vol. 221, pp. 1310–1312, 1983. The apparatus consisted of an illuminated room and a dark room, and their floors were made of stainless-steel grid. The rats placed in the illuminated room could freely enter the dark room. Upon entering the dark room the rats received an electro-shock. Retention of passive avoidance behavior to the electro-shock was determined by the measurement of a response latent period, i.e. period required for the rat experienced the electro-shock to reenter the dark room from the time on which the rat was placed in the illuminated room after predetermined intervals.

The rats received an electro-shock (0.5 mA) after one hr. from the administration of the peptides of the invention or a physiological saline solution. Immediately after receiving the electro-shock, the rats were treated with 2.7 to 3.0 mg/kg of cycloheximide or the saline solution by subcutaneous injection. At 48 hours after the administration was made, memory retentions of the rats were tested. The rats administered with only the physiological saline solution showed the response latent period of approx. 300 seconds, and those rats of control group administered with a physiological saline and treated with cycloheximide alone showed the response latent period of approx. 50 seconds, which revealed retrograde amnesia.

The average response latent period of rats administered with each peptide derivative of the invention were compared with that of control groups. Six to eight rats were used for each group to be tested. The response latent period was measured up to a maximum of 600 seconds.

The dose and the effect (the ratio of response latent period of each group to that of the control groups, shown as %) of the peptides obtained in each example and the peptides of each comparison example are set forth in Table 1.

TABLE 1

| Compound | Dose (ng/kg) | Effect (%) |
| --- | --- | --- |
| Example 1 | 0.1 | 296 |
| Example 2 | 0.01 | 235 |
| Example 3 | 1 | 214 |
| Example 4 | 1 | 240 |
| Example 5 | 0.1 | 221 |
| Example 6 | 1 | 247 |
| Example 7 | 0.01 | 249 |
| Example 8 | 0.1 | 281 |
| Example 9 | 10 | 213 |

As is readily apparent from the above experimental results, the peptides derivative of the invention had the same effects as the known peptides having the thiamine group at a dose of 1/10 to 1/100 to that of the known peptides and showed superior effect on the facilitation of memory consolidations well as effect on improving retrograde amnesia.

PREPARATION EXAMPLE 1

Injection

To 100 ml of a distilled water for injection were added 0.1 mg of the peptide obtained in Example 1 and 0.9 g of sodium chloride to prepare an aqueous solution whose pH was adjusted to 6.0 to 8.0 with sodium hydroxide. The solution was filtered under sterile condition, and the filtrate was filled up into 1 ml ampul. The ampul was fused to seal under sterile condition by heating to prepare an agent for injection.

PREPARATION EXAMPLE 2

Freeze-Dried Agent

To 100 ml of a distilled water for injection were added 5 mg of the peptide obtained in Example 1 and 5 g of D-mannitol to prepare an aqueous solution of which pH was adjusted to 6.0 to 8.0 with a phosphate buffer. The solution was filtered under sterile condition and the filtrate was divided into a plurality of 1 ml vials. The divided portions were freeze-dried to prepare a freeze-dried agent for injection.

PREPARATION EXAMPLE 3

Collunarium

To 100 ml of a physiological saline solution was added 10 mg of the peptide obtained in Example 1. The pH of the mixture was adjusted to 3.0 to 6.0 with a citric acid buffer to prepare a collinarium which contains 50 μg of the peptide of the invention in a dose of 0.5 ml.

PREPARATION EXAMPLE 4

Suppository

To 98.5 g of hard fat (triglyceride of saturated fatty acid) was added 0.5 of egg yolk lecithin. The mixture was melted at temperature of 40° to 45° C. and to the melted mixture was added under stirring a solution of 5 mg of the peptide (obtained in Example 1) in 1 g of Polyethylene glycol (PEG) 400. The resulting dispersion (1 g) was filled into the mold for suppository. The content was removed from the mold after being caked to prepare a suppository.

We claim:

1. A peptide derivative having the formula (I):

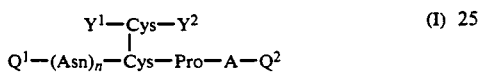
(I)

wherein

A between Pro and Q² is Arg or Lys: Q¹ is pGlu or H; Q² is -Gly-OH or OH; Y¹ is H or —CO—T and Y² is OH or T;

wherein

T represents a group having the formula (II):

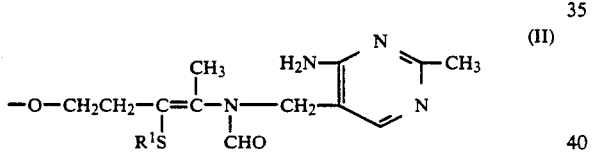
(II)

wherein $R^1$ is a group selected from the group consisting of an alkylcarbonyl group having 2 to 7 carbon atoms, an arylcarbonyl group having 7 to 10 carbon atoms, and an alkylthio group having 1 to 6 carbon atoms; or a group having the formula (III):

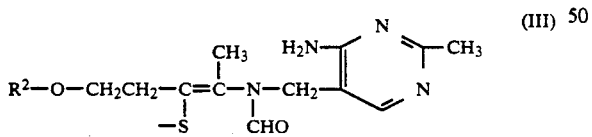
(III)

wherein $R^2$ is a group selected from the group consisting of hydrogen, an alkylcarbonyl group having 2 to 7 carbon atoms, and an arylcarbonyl group having 7 to 10 carbon atoms;

wherein at least either Y¹ is —CO—T, or Y² is T, n is 0 or 1; and amino acids constituting the peptide are those of type L with the proviso that both Pro and Arg are of type D;

or functional derivatives of said peptide derivative selected from the group consisting of N-acyl derivatives having a group of —NHCOR wherein R is an alkyl group of 1-5 carbon atoms, a derivative in the form of amide, a monoalkyl-substituted amide or dialkyl-substituted amide derivative respectively, represented by —CONH₂, —CONHR or —CONR₂ wherein R is an alkyl group of 1-6 carbon atoms, or a derivative in the form of ester represented by —COOR wherein R is an alkyl group of 1-18 carbon atoms, at least one functional group or a pharmaceutically acceptable salt.

2. The peptide derivative as claimed in claim 1, wherein Y¹ and Y² of the formula (I) are H and T, respectively.

3. The peptide derivative as claimed in claim 1, wherein the peptide derivative has one of the following formulae:

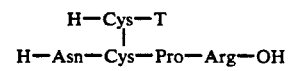

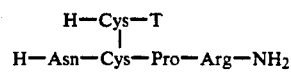

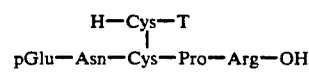

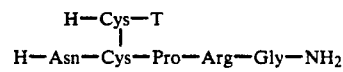

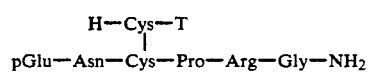

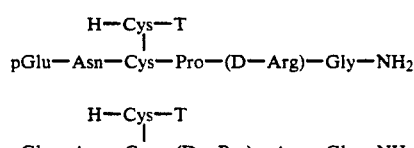

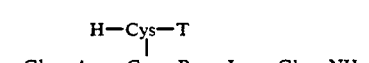

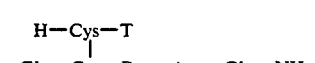

their functional derivatives or pharmaceutically acceptable salts.

4. A composition comprising an antidementia effective amount of the peptide derivative, functional derivative or salt of claim 1 and a pharmaceutically acceptable carrier therefore.

5. A composition comprising an antidementia effective amount of the peptide derivative, functional derivative or salt of claim 2 and a pharmaceutically acceptable carrier therefore.

6. A composition comprising an antidementia effective amount of the peptide derivative, functional derivative or salt of claim 3 and a pharmaceutically acceptable carrier therefore.

7. The composition of claim 4 in the form of an injectable liquid, a collunarium or a suppository.

8. The peptide derivative of claim 1 wherein n is 1.

9. The anti-dementia composition of claim 4 wherein n is 1.

* * * * *